US012616653B2

(12) United States Patent
Dellera et al.

(10) Patent No.: US 12,616,653 B2
(45) Date of Patent: May 5, 2026

(54) SOLID ORODISPERSIBLE PHARMACEUTICAL COMPOSITION IN FILM CONTAINING LORAZEPAM

(71) Applicant: Altergon S.A., Lugano (CH)

(72) Inventors: Eleonora Dellera, Lugano (CH); Andrea Giori, Lugano (CH); Roberta Lollini, Lugano (CH); Fabio Marra, Milan (IT)

(73) Assignee: Altergon S.A., Lugano (CH)

( * ) Notice: Subject to any disclaimer, the term of this patent is extended or adjusted under 35 U.S.C. 154(b) by 441 days.

(21) Appl. No.: 18/548,338

(22) PCT Filed: Mar. 1, 2022

(86) PCT No.: PCT/IB2022/051793

§ 371 (c)(1),
(2) Date: Aug. 30, 2023

(87) PCT Pub. No.: WO2022/185201

PCT Pub. Date: Sep. 9, 2022

(65) Prior Publication Data

US 2024/0156725 A1 May 16, 2024

(30) Foreign Application Priority Data

Mar. 2, 2021 (IT) ........................ 102021000004880

(51) Int. Cl.

| | |
|---|---|
| ***A61K 9/00*** | (2006.01) |
| ***A61K 31/5513*** | (2006.01) |
| ***A61K 47/14*** | (2017.01) |
| ***A61K 47/18*** | (2017.01) |
| ***A61K 47/26*** | (2006.01) |
| ***A61K 47/34*** | (2017.01) |
| ***A61K 47/36*** | (2006.01) |
| ***A61K 47/44*** | (2017.01) |

(52) U.S. Cl.

CPC ........ *A61K 9/0056* (2013.01); *A61K 31/5513* (2013.01); *A61K 47/14* (2013.01); *A61K 47/186* (2013.01); *A61K 47/26* (2013.01); *A61K 47/34* (2013.01); *A61K 47/36* (2013.01); *A61K 47/44* (2013.01)

(58) Field of Classification Search

CPC .. A61K 9/0056; A61K 31/5513; A61K 47/14; A61K 47/186; A61K 47/26; A61K 47/34; A61K 47/36; A61K 47/44

See application file for complete search history.

(56) References Cited

U.S. PATENT DOCUMENTS

| | | | | |
|---|---|---|---|---|
| 4,371,516 | A | 2/1983 | Gregory et al. | |
| 11,123,287 | B2 * | 9/2021 | Cilurzo ................ | A61K 8/8129 |
| 2014/0335153 | A1 | 11/2014 | Allen et al. | |
| 2018/0243207 | A1 | 8/2018 | Singh | |
| 2018/0360736 | A1 | 12/2018 | Obeid et al. | |

FOREIGN PATENT DOCUMENTS

| | | | |
|---|---|---|---|
| EP | 0487520 | A1 | 6/1992 |
| WO | 2016094567 | A1 | 6/2016 |

OTHER PUBLICATIONS

Gurgel Adeodato Vieira M. et al., "Natural-based plasticizers and biopolymer films: A review", European Polymer Journal, vol. 47, No. 3, Dec. 19, 2010, pp. 254-263.

Search Report and Written Opinion of PCT/IB2022/051793 issued May 30, 2022.

Srivastava C. M. et al., "Dextrose modified flexible tasar and muga fibroin films for wound healing applications", Materials Science and Engineering C., vol. 75, Feb. 10, 2017, pp. 104-114.

* cited by examiner

*Primary Examiner* — Jeffrey S Lundgren

*Assistant Examiner* — W. Justin Youngblood

(74) *Attorney, Agent, or Firm* — Silvia Salvadori, P.C.; Silvia Salvadori

(57) ABSTRACT

Disclosed are solid orodispersible pharmaceutical compositions in film form for oral administration of lorazepam, characterised by high stability throughout the shelf life of the product. The compositions disclosed are suitable for administration even to unconscious or dysphagic patients.

12 Claims, No Drawings

SOLID ORODISPERSIBLE PHARMACEUTICAL COMPOSITION IN FILM CONTAINING LORAZEPAM

This application is a U.S. national stage of PCT/IB2022/051793 filed on 1 March 2022, which claims priority to and the benefit of Italian Patent Application No. 102021000004880 filed on 2 Mar. 2021, the contents of which are incorporated herein by reference in their entireties.

The present invention relates to a solid orodispersible pharmaceutical composition in film form for the oral administration of lorazepam. In particular, the invention describes an orodispersible film containing lorazepam, a ready-to-use pharmaceutical form, usable without water, suitable for the administration of the active ingredient even to unconscious or dysphagic patients, which can be prepared not only in the various dosages already approved, but also in dosages adaptable to the patient's therapeutic requirements and which remains stable throughout the entire shelf life of the product.

PRIOR ART

Lorazepam (7-chloro-5 -(2'-chlorophenyl-)1,3-dihydro-3-hydroxy-2H-1,4-benzo-diazepin-2-one, formula I) belongs to the benzodiazepine family, a class of medicaments which has been used for decades for the treatment of anxiety caused by depression or neurosis, insomnia and sleep disorders of various origins, treatment of psychosomatic disorders and as adjuvant in the treatment of epilepsy and neuropathic pain.

I

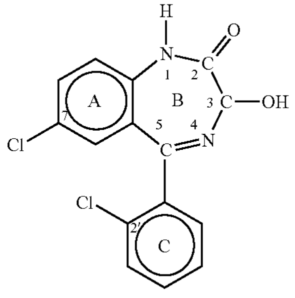

The nature of the substituent groups on the 1,4-benzodiazepine ring has an impact on the pharmacological potency. The presence of the chlorine atom in the 2' position makes lorazepam pharmacologically highly active, but the presence of the electron-acceptor atom destabilizes lorazepam, making it one of the least chemically stable benzodiazepines. The hydroxyl group present on the 7-atom ring causes a tensioning on the molecular structure, that brings to the rearrangement towards a 6-atom ring, which is much more stable and less strained, with the elimination of a water molecule (Scheme 1). This lorazepam rearrangement/dehydration process is promoted by temperature increase and is responsible for the formation of quinazoline aldehyde, identified in the USP monograph as Impurity C (M. S. Siddegowda et al. "Facile Thermal Rearrangement of Lorazepam and Oxazepam", Indian Journal of Chemistry Section B 51(11):1628-1632, 2012).

Scheme 1. Rearrangement of Lorazepam

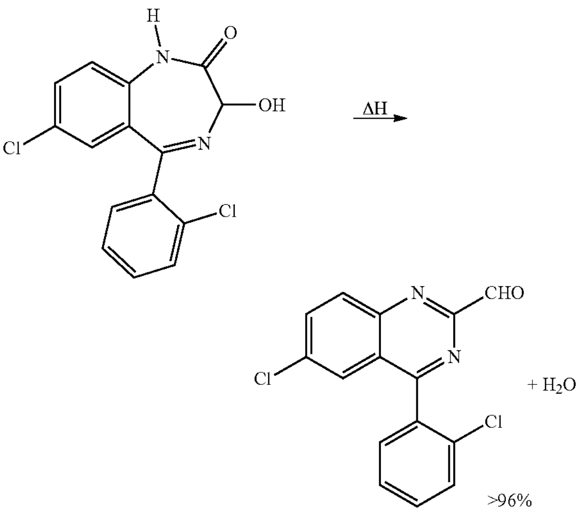

There are no ready-to-use oral solutions of lorazepam on the market, only solutions designed to be reconstituted prior to use, by solubilizing lorazepam in the mixture of solvents immediately before administration. The reconstituted solution has a shelf life limited to one month, preferably at low temperature.

WO2004004783 discloses a ready-to-use liquid oral formulation of lorazepam, which does not need to be reconstituted. The formulation overcomes the problem of the stability of lorazepam by eliminating water from the formulation and using triacetin (triacetyl glycerin), a colourless, odourless solvent described in the pharmacopoeias, combined with diethylene glycol monoethylether (commercially known as Transcutol®). WO2004004783 does not use polyalcohols, which, like all solvents containing hydroxyl groups, are considered to be responsible for the instability of lorazepam.

WO2008/019109 has already described the problems of formulating lorazepam in orodispersible pharmaceutical forms, such as orodispersible tablets (ODT). WO2008/019109 specifies that the use of common excipients for this type of pharmaceutical form, such as mannitol or polyvinylpyrrolidone (PVP), reduces the stability of the lorazepam in the finished product. The stability of the active ingredient is guaranteed in this case by protecting lorazepam with a granulation process or coating it with a polymer having a glass transition temperature ($T_g$) exceeding 65° C., preferably cellulose derivatives or PVP.

US2016/0000803 discloses a liquid formulation for nasal administration of benzodiazepines, including lorazepam. It makes no reference to the poor chemical stability of lorazepam, but aims to overcome the poor solubility of lorazepam which causes its precipitation in water and in hydrophobic solvents. Therefore, it is impossible to obtain concentrated solutions which can be administered in small volumes suitable for the small size of the nasal cavities. US2016/0000803 overcomes the problem by including in the emulsions substances which form eutectic mixtures with benzodiazepines (menthol, thymol).

Ready-to-use oral solutions and ODTs are very convenient pharmaceutical forms which are useful in specific clinical applications of benzodiazepines, in particular lorazepam, such as the treatment of patients suffering from epileptic fits, for whom the fastest possible administration is required.

Among the fast-dissolving oral forms, orodispersible films (ODFs) have recently attracted increasing interest. Said films are thin sheets designed to be introduced into the oral cavity, contain the active ingredient, either dispersed or dissolved, and consist of film-forming polymers and other excipients used to obtain a dosage form suitable for oral administration. Oral films are generally prepared by dissolving the film-forming polymer, such as cellulose, maltodextrins or alginates, in a suitable solvent, such as water or ethanol. Plasticizers must be introduced in addition to the film-forming polymer, in order to obtain strong and flexible films and guarantee adequate mechanical properties. Plasticizers generally belong to the chemical class of polyalcohols, which are also considered as polar solvents.

Compared with oral solutions, which must be prepared and dosed at the time of use, the films are ready to use and ensure a precise and wide range of dosages. Unlike the conventional solid forms, they can be taken without swallowing and without water, leave no residues in the mouth after their very fast disintegration and therefore do not involve the risk that uncooperative patients will expel any fragments, as can occur with tablets which are not swallowed or fail to fully disintegrate. When introduced into the mouth and placed on the tongue, they disintegrate rapidly in contact with the saliva, thus enabling the active ingredient to be administered without further liquids. Unlike ODTs, the fragments deriving from film disintegration are very small and difficult to expel. This constitutes an advantage in the case of urgent administration when epileptic seizures occur.

The particularly unstable nature of lorazepam makes it difficult to formulate an oral film that preserve its physicochemical stability and is also reproducible with an industrial process. From the pharmaceutical standpoint, a product is deemed stable and suitable for marketing if it meets the requirements of the pharmacopoeias, guarantees compliance with the specifications for a suitable period of time and allows practical storage conditions, for example at room temperature.

The excipients commonly used in oral film preparation are among the substances responsible for the degradation of lorazepam, in particular polar solvents such as water or ethanol, lipophilic solvents and plasticizers such as glycerin polyalcohols and propylene glycol.

WO2005039543 and WO2014049548 disclose oral film formulations wherein lorazepam degrades rapidly, as will be demonstrated in the examples set out in the description of the invention.

DESCRIPTION OF THE INVENTION

The present invention overcomes the problems described above, allowing lorazepam to be formulated in a fast-disintegrating film, which is stable over time and able to provide a product with adequate mechanical properties.

It has been found that, contrary to the expectations deriving from the known destabilising effects of water and lipophilic solvents, lorazepam can be formulated as stable orodispersible films by combining a film-forming agent, prepared with water as solvent, with a plasticizer that is solid at room temperature and a pharmaceutical-grade oil.

A first aspect of the invention therefore relates to a solid orodispersible pharmaceutical composition in fast-disintegrating film form comprising lorazepam, at least one film-forming polymer selected from maltodextrins, copovidone, sodium alginate or mixtures thereof and at least one plasticizer, characterised in that the plasticizers are only those in solid form at room temperature and in that the composition comprises water and a pharmaceutical-grade non-essential oil.

"Fast disintegration" here means that the film disperses in the oral cavity to release the active ingredient rapidly (Ph. Eur. current edition, 1807 Oromucosal Preparations, orodispersible films), i.e. within 3 minutes (Ph. Eur. 0478, Tablets, Orodispersible Tablets), preferably within 1 minute after administration.

The compositions according to the invention can be prepared by a process which comprises adding a dispersion of lorazepam in pharmaceutical-grade oil to an aqueous solution of the hydrophilic ingredients (film-forming agent and solid plasticizer), continuous drying of the mixture and cutting the resulting film to size.

The plasticizer which is solid at room temperature is selected from polyalcohols (such as sorbitol, mannitol, maltitol and xylitol) and betaine. The solid plasticizer is present in percentages ranging from 5 to 50% by weight, preferably from 10 to 30%.

The film-forming polymer is present in percentages ranging from 40 to 80% by weight.

The water in the films according to the invention is present in percentages ranging from 5 to 30% by weight.

"Non-essential oil" here means an oil that does not belong to the category of essential oils, which are defined as an odorous product, usually of complex composition, obtained from a botanically defined plant raw material by steam distillation, dry distillation, or a suitable mechanical process without heating, and optionally subjected to further treatments to modify its chemical composition (Ph. Eur. current edition, 2098 Essential Oils).

The non-essential oil is selected from vegetable or animal oils or medium-chain triglycerides and is present in percentages ranging from 1 to 15% by weight.

Olive, sesame, sunflower, soybean, peanut, corn, safflower or fish oil are preferably used.

Lorazepam is present in percentages ranging from 0.25 to 10% by weight.

The compositions according to the invention can also contain other excipients, such as surfactants and other ingredients required to improve the organoleptic properties of the film, such as flavourings, sweeteners, colourings and the like. No plasticizers which are liquid at room temperature, such as glycerol, can be present.

Surprisingly, the films according to the invention are more stable over time despite the presence of residual water in the film. Lorazepam is homogeneous in the films, even if solvents wherein it is poorly soluble, such as water or pharmaceutical-grade oils, are used.

The invention is illustrated in greater detail in the examples below.

COMPARATIVE EXAMPLE 1

The oral film of the Example, formulation 1, was prepared according to WO2014049548. Formulation 1 is shown in Table 1.

TABLE 1

| Formulation 1, expressed as % w/w | | |
|---|---|---|
| Ingredient | Function | Composition (%) |
| Lorazepam | Active ingredient | 2.00 |
| Maltodextrins | Film-forming polymer | 63.798 |

TABLE 1-continued

| Formulation 1, expressed as % w/w | | |
|---|---|---|
| Ingredient | Function | Composition (%) |
| Glycerol | Plasticizer | 15.00 |
| Water | Solvent residue | 10.00 |
| Mannitol | Plasticizer | 5.00 |
| Copovidone | Film-forming polymer | 2.00 |
| Glycerol monolinoleate | Surfactant | 1.12 |
| Polysorbate 80 | Surfactant | 0.38 |
| Sucralose | Sweetener | 0.20 |
| Titanium dioxide | Colouring | 0.50 |
| Brilliant Blue FCF E133 | Colouring | 0.002 |

Briefly, to prepare formulation 1, lorazepam is pre-dispersed in glycerin; said mixture is then added to the other ingredients, pre-solubilized in water, and the mass is mixed until completely homogeneous. The mixture is coated and dried continuously until a uniform, bubble-free roll of film is obtained. The roll is cut to suitable dimensions to obtain films with the required doses.

The assay value and degradation products were analysed by HPLC. The column was an ACE Equivalence C18 (250 mm×4.6 mm) with a particle size of 5 μm, thermostated to 10° C. A 50:50 mixture of an 0.24% aqueous solution of acetic acid and acetonitrile was used as mobile phase, at a flow rate of 1.0 ml/minute. The DAD-UV detector was set to 230 nm, and 10 μl of sample were injected.

The long-term stability study (25° C., 60% R/H), intermediate stability study (30° C., 65% R/H) and accelerated stability study (40° C., 75% R/H) confirmed that lorazepam is highly instable, as summarised in Table 2. In just three months the assay value falls by 7.5% at 25° C., 12.4% at 30° C. and 55.4% at 40° C. The drastic reduction in assay value is accompanied by a significant increase in Impurity C content, which reaches 35.97% in three months at 40° C. At 25° C. and 30° C. the percentage of Impurity C is much lower, but still above the 3.0% limit set in the USP monograph for Lorazepam Tablets.

TABLE 2

| Assay value of lorazepam and Impurity C content in formulation 1 in stability tests | | | | | |
|---|---|---|---|---|---|
| Test | Conditions | T0 | 15 days | 1 month | 3 months |
| Assay value | 25° C., 60% R/H | 104.9% | 101.6% | 101.6% | 97.4% |
| | 30° C., 65% R/H | | 103.8% | 100.3% | 92.5% |
| | 40° C., 75% R/H | | 99.2% | 100.3% | 49.5% |
| Impurity C | 25° C., 60% R/H | 0.23% | 0.82% | 1.51% | 3.52% |
| | 30° C., 65% R/H | | 1.23% | 2.54% | 8.14% |
| | 40° C., 75% R/H | | 4.01% | 11.44% | 35.97% |

These data demonstrate that the oral film with lorazepam, obtained according to WO2014049548, does not meet the specifications set out in the USP monograph, as the percentage of Impurity C exceeds the specification of 3.0%. The formulation is therefore not stable, even at room temperature.

EXAMPLE 2

The formulations according to the invention are shown in Table 3.

TABLE 3

| Formulations of lorazepam films, expressed as % w/w. | | | |
|---|---|---|---|
| | | Composition (%) | |
| Ingredient | Function | Formulation 2 | Formulation 3 |
| Lorazepam | Active ingredient | 2.00 | 2.00 |
| Maltodextrins | Film-forming polymer | 64.498 | 66.498 |
| Copovidone | Film-forming polymer | 2.00 | — |
| Water | Solvent residue | 12.50 | 12.50 |
| Anhydrous betaine | Plasticizer | 7.50 | 7.50 |
| Mannitol | Plasticizer | 5.00 | 5.00 |
| Refined olive oil | Lipophilic solvent | 5.00 | 5.00 |
| Titanium dioxide | Colouring | 0.50 | 0.50 |
| Oleoyl macrogol-6 glycerides | Surfactant | 0.50 | 0.50 |
| Polyglyceryl-3 dioleate | Surfactant | 0.50 | 0.50 |
| Brilliant Blue FCF E133 | Colouring | 0.002 | 0.002 |

To prepare the films according to the invention, lorazepam is dispersed in pharmaceutical-grade olive oil; in the meantime, the aqueous solution of the hydrophilic ingredients is prepared and the oily mixture containing lorazepam is added under continuous stirring. The resulting mass is mixed until completely homogeneous, then coated and dried continuously until a uniform, bubble-free roll of film is obtained. The roll is cut to suitable dimensions to obtain films with the required doses.

The films appear plastic, strong and disintegrate rapidly (10 seconds), using the disintegration test according to the European Pharmacopoeia (Ph. Eur., 2.9.1) for solid oral forms.

The assay value and degradation products were analysed by the method described in Example 1.

The results of the long-term stability study (25° C., 60% R/H), intermediate stability study (30° C., 65% R/H) and accelerated stability study (40° C., 75% R/H) are shown in Table 4.

Unlike the results observed for the formulation according to Comparative Example 1, the present invention surprisingly gives rise to oral films containing lorazepam with adequate stability over time. Table 4 shows the stability data of formulations 2 and 3 obtained according to the invention, up to 3 months.

TABLE 4

Assay value of lorazepam and Impurity C content in formulations 2 and 3 in stability tests

| Formula | Test | Conditions | T0 | 1 month | 2 months | 3 months |
|---|---|---|---|---|---|---|
| Formulation 2 | Assay value | 25° C., 60% R/H | 101.2% | 100.9% | 102.6% | 100.3% |
| | | 30° C., 65% R/H | | 98.4% | 99.5% | 101.1% |
| | | 40° C., 75% R/H | | 97.9% | 92.1% | 85.5% |
| | Impurity C | 25° C., 60% R/H | 0.26% | 0.32% | 0.37% | 0.54% |
| | | 30° C., 65% R/H | | 0.65% | 0.77% | 0.98% |
| | | 40° C., 75% R/H | | 2.15% | 2.82% | 4.62% |
| Formulation 3 | Assay value | 25° C., 60% R/H | 99.7% | 105.0% | 104.2% | 100.2% |
| | | 30° C., 65% R/H | | 101.2% | 100.4% | 100.8% |
| | | 40° C., 75% R/H | | 97.1% | 96.4% | 85.4% |
| | Impurity C | 25° C., 60% R/H | ND | 0.51% | 0.36% | 0.43% |
| | | 30° C., 65% R/H | | 0.41% | 0.71% | 0.85% |
| | | 40° C., 75% R/H | | 1.99% | 2.26% | 3.62% |

ND=percentage below detectability limit

If the variations in the assay value of lorazepam and Impurity C during the stability studies are compared, it will be seen that the films according to the invention are significantly more stable, especially when compared with the results of Comparative Example 1. The assay value of lorazepam in formulations 2 and 3 is practically unchanged at 25° C. and 30° C. At 40° C. a significant reduction is observed, but lower when compared with Comparative Example 1: after 3 months in this latter case, there was a reduction exceeding 50%, whereas in the formulas according to Example 2, the reduction was about 15%.

The consequence of these limited variations in assay value is a less significant increase in Impurity C, especially at 25° C. and 30° C. Under these storage conditions, the values are below the 3.0% limit taken as reference. At 40° C., after 3 months, the value of Impurity C is out of specification, but in both formulations according to the invention the percentage is surprisingly about 10 times lower than the percentage found in Comparative Example 1 (35.97%).

EXAMPLE 3

Other formulations according to the invention are shown in Table 5.

TABLE 5

Formulations of lorazepam films, expressed as % w/w.

| Ingredient | Function | Composition (%) Formulation 4 | Formulation 5 |
|---|---|---|---|
| Lorazepam | Active ingredient | 2.00 | 2.00 |
| Maltodextrins | Film-forming polymer | 46.396 | 46.396 |
| Sodium alginate | Film-forming polymer | 10.00 | 10.00 |
| Water | Solvent residue | 15.00 | 15.00 |
| Anhydrous betaine | Plasticizer | 10.00 | 10.00 |
| Mannitol | Plasticizer | 10.00 | — |
| Sorbitol | Plasticizer | — | 10.00 |
| Refined olive oil | Lipophilic solvent | 5.00 | 5.00 |
| Titanium dioxide | Colouring | 0.50 | 0.50 |
| Oleoyl macrogol-6 glycerides | Surfactant | 0.50 | 0.50 |
| Polyglyceryl-3 dioleate | Surfactant | 0.50 | 0.50 |
| Sucralose | Sweetener | 0.10 | 0.10 |
| Brilliant Blue FCF E133 | Colouring | 0.004 | 0.004 |

In order to prepare the films according to the invention, lorazepam is dispersed in pharmaceutical-grade olive oil; in the meantime the aqueous solution of the hydrophilic ingredients is prepared and the oily mixture with lorazepam is added under continuous stirring. The resulting mass is mixed until completely homogeneous. The mixture is continuously spread and dried until a uniform, bubble-free roll of film is obtained. The roll is cut to suitable dimensions to obtain films with the required doses. For example, a 1 mg lorazepam film has a size of 20 mm×15 mm, and a weight of 50 mg; a 2.5 mg lorazepam film has a size of 30 mm×25 mm, and a weight of 125 mg.

The films appear plastic, strong and disintegrate rapidly (10 seconds), using the disintegration test according to the European Pharmacopoeia (Ph. Eur., 2.9.1) for solid oral forms.

The analyses of the assay value and the degradation products were conducted by the method described in Comparative Example 1.

The results of the long-term stability study (25° C., 60% R/H), intermediate stability study (30° C., 65% R/H) and accelerated stability study (40° C., 75% R/H) of formulations 4 and 5 up to 3 months are shown in Table 6. Unlike the results obtained with the formulations according to Example 1, the formulations according to the invention exhibit adequate stability over time.

TABLE 6

Assay value of lorazepam and Impurity C content in formulations 4 and 5 in stability tests

| Formula | Test | Conditions | T0 | 1 month | 2 months | 3 months |
|---|---|---|---|---|---|---|
| Formulation 4 | Assay value | 25° C., 60% R/H | 104.5% | 105.0% | 104.6% | 105.0% |
| | | 30° C., 65% R/H | | 105.0% | 103.3% | 104.4% |
| | | 40° C., 75% R/H | | 104.1% | 97.3% | 94.6% |
| | Impurity C | 25° C., 60% R/H | 0.32% | 0.38% | 0.68% | 0.69% |
| | | 30° C., 65% R/H | | 0.43% | 0.84% | 1.11% |
| | | 40° C., 75% R/H | | 1.02% | 3.34% | 3.92% |
| Formulation 5 | Assay value | 25° C., 60% R/H | 105.0% | 98.0% | 104.4% | 104.9% |
| | | 30° C., 65% R/H | | 105.0% | 103.5% | 102.9% |
| | | 40° C., 75% R/H | | 103.9% | 91.0% | 92.3% |
| | Impurity C | 25° C., 60% R/H | ND | ND | 0.45% | 0.54% |
| | | 30° C., 65% R/H | | 0.50% | 0.83% | 1.07% |
| | | 40° C., 75% R/H | | 1.13% | 4.47% | 3.43% |

ND = percentage below detectability limit

The invention claimed is:

1. Solid orodispersible pharmaceutical composition in fast-disintegrating film form comprising lorazepam, one or more film-forming polymers selected from maltodextrins, copovidone, sodium alginate or mixtures thereof, and one or more plasticizers, wherein the plasticizers are exclusively plasticizers in solid form at room temperature and the composition comprises water and a pharmaceutical-grade non-essential oil.

2. Composition according to claim 1, wherein the plasticizers are selected from polyalcohols and betaine.

3. Composition according to claim 2, wherein the polyalcohol is selected from sorbitol, mannitol, maltitol and xylitol.

4. Composition according to claim 1, wherein the solid plasticizers are present in percentages ranging from 5 to 50% by weight.

5. Composition according to claim 1, wherein the film-forming polymer is a mixture of maltodextrins with copovidone or sodium alginate.

6. Composition according to claim 1, wherein the film-forming polymer is present in percentages ranging from 40 to 80% by weight.

7. Composition according to claim 1, wherein water is present in percentages ranging from 5 to 30% by weight.

8. Composition according to claim 1, wherein the non-essential oil is of vegetable or animal origin or a medium-chain triglyceride.

9. Composition according to claim 1, wherein the non-essential oil is selected from olive, sesame, sunflower, soybean, peanut, corn, safflower and fish oil.

10. Composition according to claim 8, wherein the non-essential oil is present in percentages ranging from 1 to 15% by weight.

11. Composition according to claim 1, wherein lorazepam is present in percentages ranging from 0.25 to 10% by weight.

12. Composition according to claim 1, wherein the solid plasticizers are present in percentages ranging from 10 to 30%.

* * * * *